United States Patent
Grillo Fernandez et al.

(10) Patent No.: US 10,219,790 B2
(45) Date of Patent: Mar. 5, 2019

(54) AUTOMATIC DEVICE FOR SKIN BIOPSIES

(71) Applicants: Universidad Carlos III De Madrid, Madrid (ES); Fundacion Para La Investigacion Biomedica Del Hospital Universitario Ramon Y Cajal, Madrid (ES)

(72) Inventors: Emiliano Grillo Fernandez, Madrid (ES); Sergio Vano Galan, Madrid (ES); Pedro Jaen Olasolo, Madrid (ES); Cristina Castejon Sisamon, Madrid (ES); Jesus Meneses Alonso, Madrid (ES); Juan Carlos Garcia Prada, Madrid (ES); Higinio Rubio Alonso, Madrid (ES)

(73) Assignee: UNIVERSIDAD CARLOS III DE MADRID, Madrid (ES)

( * ) Notice: Subject to any disclaimer, the term of this patent is extended or adjusted under 35 U.S.C. 154(b) by 391 days.

(21) Appl. No.: 15/035,986

(22) PCT Filed: Nov. 11, 2014

(86) PCT No.: PCT/ES2014/070835
§ 371 (c)(1),
(2) Date: Jul. 12, 2016

(87) PCT Pub. No.: WO2015/071516
PCT Pub. Date: May 21, 2015

(65) Prior Publication Data
US 2016/0354065 A1    Dec. 8, 2016

(30) Foreign Application Priority Data
Nov. 12, 2013   (ES) .................... 201331644

(51) Int. Cl.
*A61B 10/00* (2006.01)
*A61B 10/02* (2006.01)
(Continued)

(52) U.S. Cl.
CPC .... *A61B 10/0266* (2013.01); *A61B 17/32053* (2013.01); *A61B 2010/0208* (2013.01); *A61B 2017/00747* (2013.01)

(58) Field of Classification Search
CPC . A61B 10/00; A61B 10/02; A61B 2010/0208; A61B 20/0233
(Continued)

(56) References Cited

U.S. PATENT DOCUMENTS

| 4,469,109 A | * | 9/1984 | Mehl .................... A61B 10/025 |
| | | | 600/566 |
| 2004/0167430 A1 | | 8/2004 | Roshdieh et al. |

(Continued)

FOREIGN PATENT DOCUMENTS

| WO | 2011073725 A1 | 6/2011 |
| WO | 2013166443 A1 | 11/2013 |

*Primary Examiner* — May A Abouelela
*Assistant Examiner* — David Joseph Fernandez-Fidalgo
(74) *Attorney, Agent, or Firm* — Hayes Soloway PC

(57) ABSTRACT

The invention relates to an automatic device for performing skin biopsies, comprising a casing (2) housing a rod (3) on the distal end (3a) of which there is a circular blade (4), and means for causing simultaneous rotation and longitudinal advancement of the rod (3) from a first retracted position wherein the blade (4) of the rod (3) does not project via the distal end (2a) of the casing (2), to a second extended position wherein the blade (4) of the rod (3) projects via the distal end (2a) of the casing, followed by simultaneous rotation and longitudinal retraction of said rod (3) from said second extended position to said first retracted position.

9 Claims, 5 Drawing Sheets

(51) Int. Cl.
*A61B 17/3205* (2006.01)
*A61B 17/00* (2006.01)

(58) Field of Classification Search
USPC .......................................... 600/562, 564–568
See application file for complete search history.

(56) References Cited

U.S. PATENT DOCUMENTS

| | | |
|---|---|---|
| 2005/0267502 A1* | 12/2005 | Hochman .......... A61B 17/3211 606/167 |
| 2007/0123973 A1 | 5/2007 | Roth et al. |
| 2007/0232954 A1* | 10/2007 | Harris .................... A61B 10/02 600/564 |
| 2009/0018467 A1 | 1/2009 | Chiu et al. |
| 2012/0065096 A1 | 10/2012 | Mendez-Coll |
| 2013/0096458 A1 | 4/2013 | Schraga |

\* cited by examiner

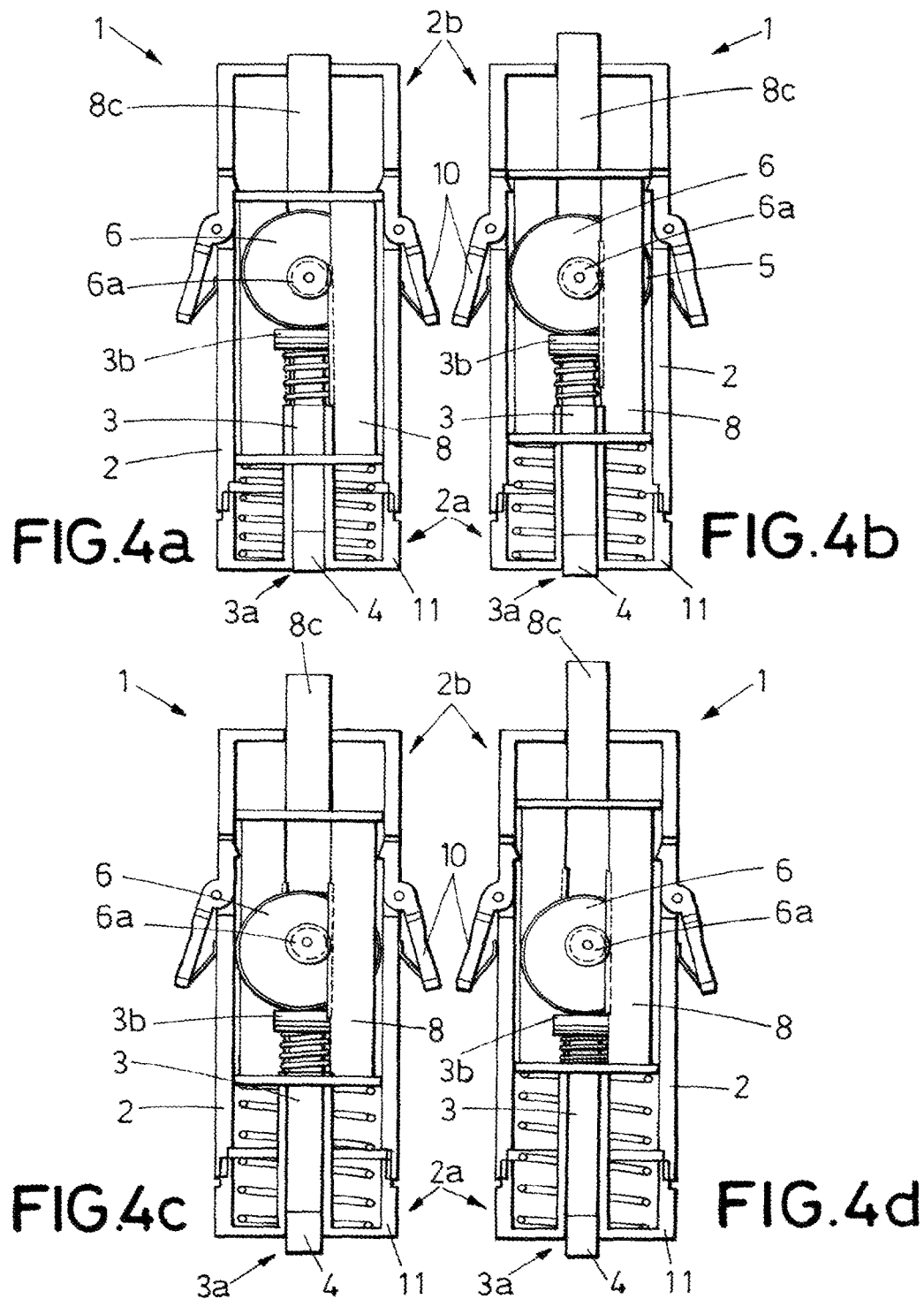

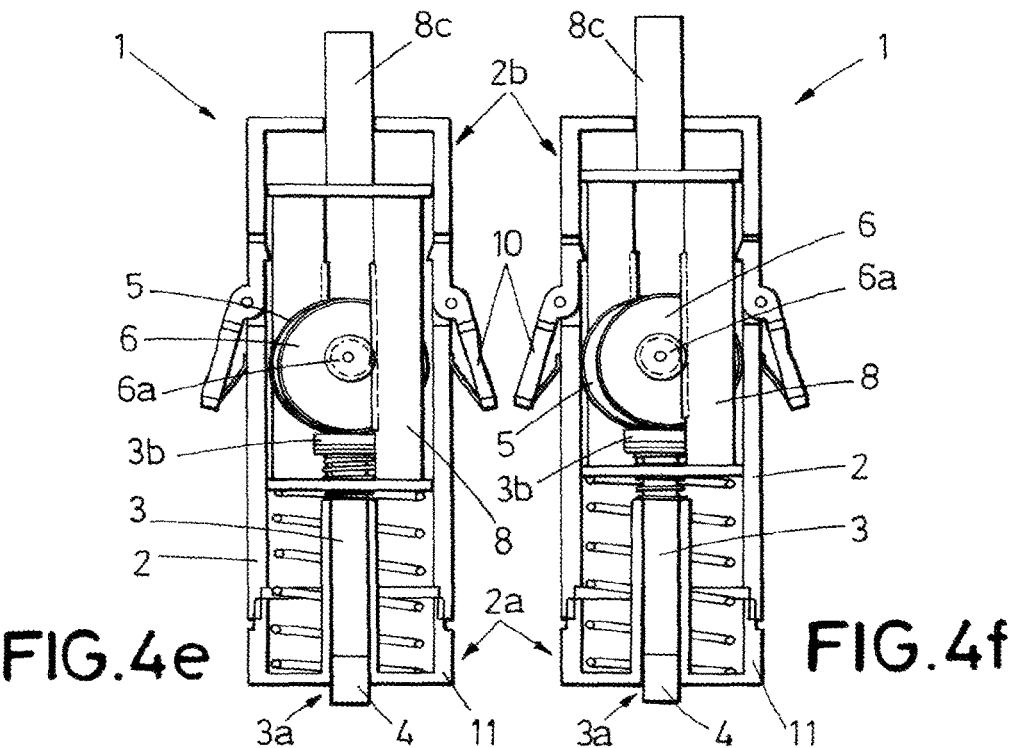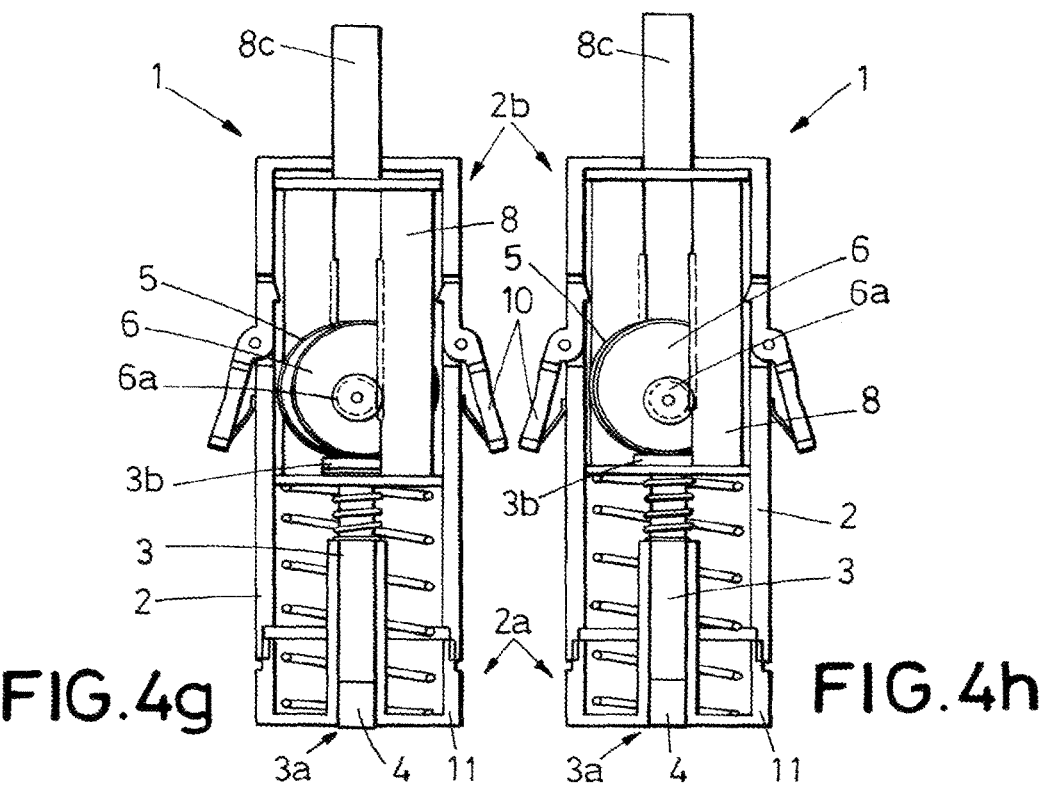

AUTOMATIC DEVICE FOR SKIN BIOPSIES

OBJECT OF THE INVENTION

This invention is in the field of medicine, more specifically in the field of medical devices used for taking cutaneous biopsies.

The invention describes a new device that enables performing a large part of the cutaneous sample extraction process in an automated way. This device enables standardisation of the process of taking a biopsy, minimising the time spent and making it accessible to staff with less specialised training.

BACKGROUND OF THE INVENTION

Performing cutaneous biopsies is a routine practice in dermatology and other specialities. A cutaneous biopsy mainly consists in the cutting and extraction of a small portion of cutaneous tissue from a patient.

Currently, the device used for performing a cutaneous biopsy mainly consists of a long cylinder that has a proximal end furnished with a handle and a distal end furnished with a cylindrical blade. To use it, the cylindrical blade of the device is pressed against the patient's skin and a circular movement is performed. This causes the cylindrical blade to pierce the patient's skin and penetrate it a certain distance. Then it is necessary to withdraw the device, cut the base of the portion of skin using a scalpel, and withdraw the sample with the help of tweezers. Finally, one or two stitches are applied to the cutaneous wound made.

This known device has numerous drawbacks. To perform a biopsy with this device, it is necessary to apply local anaesthesia and use surgical material to cut the cutaneous sample and to suture the wound, as well as a trolley bed and a side table on which to place this surgical material. Thus, with the devices of the state of the art, it is necessary to: know the prior history of anaesthesia of the patient, have a restricted sterile field, perform disinfection, inject the anaesthetic, perform another disinfection, have the instrument available to be used for the biopsy, have a scalpel for cutting the fragment of base skin and some tweezers to hold it to enable the cutting, have a gauze to dry the area and have the necessary items for suturing and dressing the wound. Also required are a trolley table and a side table on which to place the auxiliary materials.

Another drawback related to the use of this type of device is that the proper execution of the technique is very dependent on the skill of the surgeon. In fact, depending on the force applied, the speed of rotation and the type of tissue that is being pierced, the distance of penetration can vary and can even injure the patient.

Ultimately, performing cutaneous biopsies is one of the main reasons for delays in dermatology consultations. The time to perform a cutaneous biopsy is around 20 to 30 minutes during which all the necessary materials must be prepared and the test performed. Often, the option of performing this valuable diagnostic and sometimes therapeutic test is discarded due to lack of time, especially in the outpatient department. By way of example, it can be claimed that one of the most frequent causes of claims in countries such as the United States is not performing biopsies in pathologies when diagnosis is uncertain.

In fact, for reasons of time, limited space, financial cost and patient comfort, it is essential to create a device for performing this diagnostic test that is rapid, simple, safe and cheap.

DESCRIPTION OF THE INVENTION

The device of the invention resolves a large proportion of the previous problems because it enables performing the biopsy process automatically. This not only enables a saving of time compared to the known devices, but also standardises the process in relation to the depth of advance, speed of advance and speed of rotation of the blade. In this way, the repeatability of the biopsy process is improved, even in the case when the people performing it have limited previous experience.

The device of the invention mainly comprises a casing inside of which a rod is housed that has a cylindrical blade at its distal end for performing the piecing of the skin of the patient. Furthermore, this new device comprises means for causing the rotation and simultaneous longitudinal advance of the rod from a first retracted position, in which the blade does not project from the distal end of the casing to a second extended position in which the blade projects from the distal end of the casing, followed by a rotation and simultaneous retraction of said rod from the second extended position to the first retracted position.

Thus, it is enough to rest the casing on the skin of the patient where the biopsy is to be performed, and it is the device itself that automatically causes firstly, the advance of the rod and its rotation, the blade piecing the patient's skin to a specific distance, and then the retraction of the rod to return the blade to its initial position. It is easy to see that the use of this device enormously minimises the impact of user experience in biopsy, because it is enough to correctly calibrate the means forcausing the movement of the rod so that its distance, speed and rotation are the most appropriate in each case. Furthermore, this is a much faster process, cleaner and simpler than those currently known.

The means that cause the movement of advance and retraction of the rod can be designed in various ways via suitable mechanisms. Preferably such means comprise:

a) Means of displacement

There are means of displacement coupled to the rod that cause said rod to perform the movements of longitudinal advance and retraction at the same time as it rotates.

These means can be configured in different ways, such as for example by means of a crank-connecting rod mechanism. However, in a preferred embodiment of the invention, the means of displacement comprises two parallel cams that roll in opposite directions on two diametrically opposed points on the proximal end of the rod. In this way, on the one hand, the advance and retraction of the rod is caused by the cams rotating and changing the distance from their axis of rotation to the surface of the proximal end of the rod and on the other hand, this simultaneously causes the rotation of the rod because the two cams rotate in opposite directions.

The continuous contact between the cams and the surface of the proximal end of the rod can be ensured by various means, although in a preferred embodiment of the invention, a first longitudinal spring is used that pushes the rod in the proximal direction forcing continuous contact between said cams and the proximal end of the rod.

b) Means of actuation

The means of actuation act automatically on the means of displacement so that the latter cause the longitudinal advance and retraction of the rod. For example, in the specific case when the means of displacement are configured by cams, the means of actuation will be those responsible for causing the cams to rotate.

This can be achieved in various ways, although in a specially preferred embodiment of the invention, the means of actuation comprise a longitudinal stroke actuator coupled to pinions of the cams by means of racks. The actuator in turn is coupled to a second longitudinal spring arranged so that when the rod is in the first retracted position, the second spring is compressed. When this second spring is released, it causes a longitudinal displacement of the actuator that is transmitted via the rack gears to the cams. The rotation of the cams causes the advance and rotation of the rod from the first retracted position to the second extended position and its subsequence retraction to the first retracted position.

That is, it starts at the first retracted position in which the rod does not project from the distal end of the casing and the second spring that pushes the actuator is compressed. Next, the spring starts to push the actuator longitudinally, which causes the rack to rotate the cams, and these in turn cause the rotation and simultaneously, first the advance and later the retraction of the rod, which reaches the second extended position and then returns to the first retracted position. This mechanism will be better understood on considering the figures and the description of a particular embodiment that appears later in this document.

Preferably, the cams and the actuator are designed in such a way that a full stroke of the actuator causes a complete cycle of advance and retraction of the rod that starts and finishes in the first retracted position.

In another preferred embodiment of the invention, the actuator further comprises a loader that projects from the casing so that the user can manually move said actuator for compressing the second longitudinal spring. In a particular embodiment, the loader can project in a longitudinal direction through the proximal end of the casing, although other options are also possible. For example, the loader could project laterally from the casing and move longitudinally along a slot in the casing to move the actuator to compress the second spring.

In another preferred embodiment of the invention, the device further comprises some means of locking that engages the actuator when this compresses the second longitudinal spring. For example, the means of locking could comprise two rocking latches furnished with a pawl for the actuator.

Thus, the user can "load" the device with the help of the loader, engaging at this time the actuator by the means of locking to prevent its movement until necessary. The device remains indefinitely "loaded", with the second spring compressed and exercising force on the actuator and with the rod in the first retracted position in which it does not project.

In another preferred embodiment of the invention, the distal end of the casing comprises a threaded part that enables regulating the distance that the blade projects through the distal end of the casing when the rod is in the second extended position. That is, this part can be screwed in more or less to the rest of the casing so that when it is more threaded, the blade projects more from the casing and vice versa. In this way, the distance of penetration of the blade into the patient's skin can be regulated in order to adapt the device to different types of biopsy.

In accordance with another preferred embodiment of the invention, in the second extended position, the blade projects through the distal end of the casing by a distance of between 2 mm and 6 mm. The length of 6 mm corresponds to the situation in which the threaded part is fully screwed in to the rest of the casing, and corresponds to the maximum depth of a cutaneous biopsy without injuring the patient. The length of 2 mm corresponds to a situation in which said threaded part has been extracted (unscrewed) a length of 4 mm, and corresponds to the minimum depth that a cutaneous biopsy may reach.

Furthermore, in another preferred embodiment of the invention, the blade is attached to the rod in a detachable way, for example, by a screw. In this way, by replacing the blade and, if necessary, the threaded part that constitutes the distal end of the casing, the device can be used an indefinite number of times without compromising the patient's safety. The used blade and the threaded part are discarded and are replaced by other sterile parts.

Furthermore, the interior of the cylindrical blade is preferably in a conical form that narrows in the proximal direction. Thus, after the penetrating of the patient's skin, the cutaneous sample will be slightly compressed, which encourages its adherence by friction to the interior walls of the blade. The effect of this characteristic is that the cutaneous sample is separated from the rest of the patient's skin during the retraction of the blade in the second part of the process, avoiding the need to use tweezers and scalpel for this operation.

BRIEF DESCRIPTION OF THE FIGURES

FIGS. 4a-4h show various cross-sections of various steps representative of a cycle of advance and retraction of the device of the invention.

PREFERRED EMBODIMENT OF THE INVENTION

Figure 1:
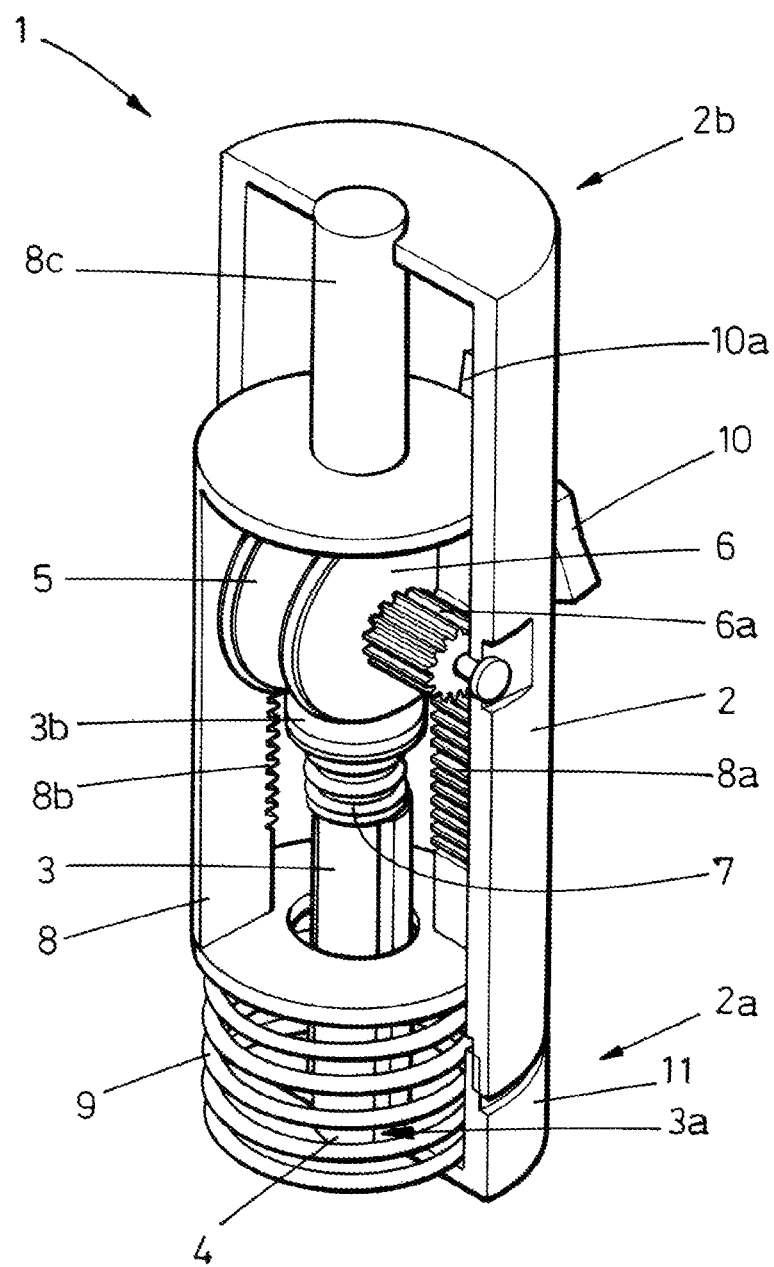
FIG. 1 shows a perspective view of the device of the invention with half the casing removed.

A particular embodiment of the invention is described below making reference to the attached figures. FIG. 1 shows a perspective view of an example of the device (1) of the invention where parts have been removed so that the remaining parts that compose it can be seen more clearly.

Figure 2:
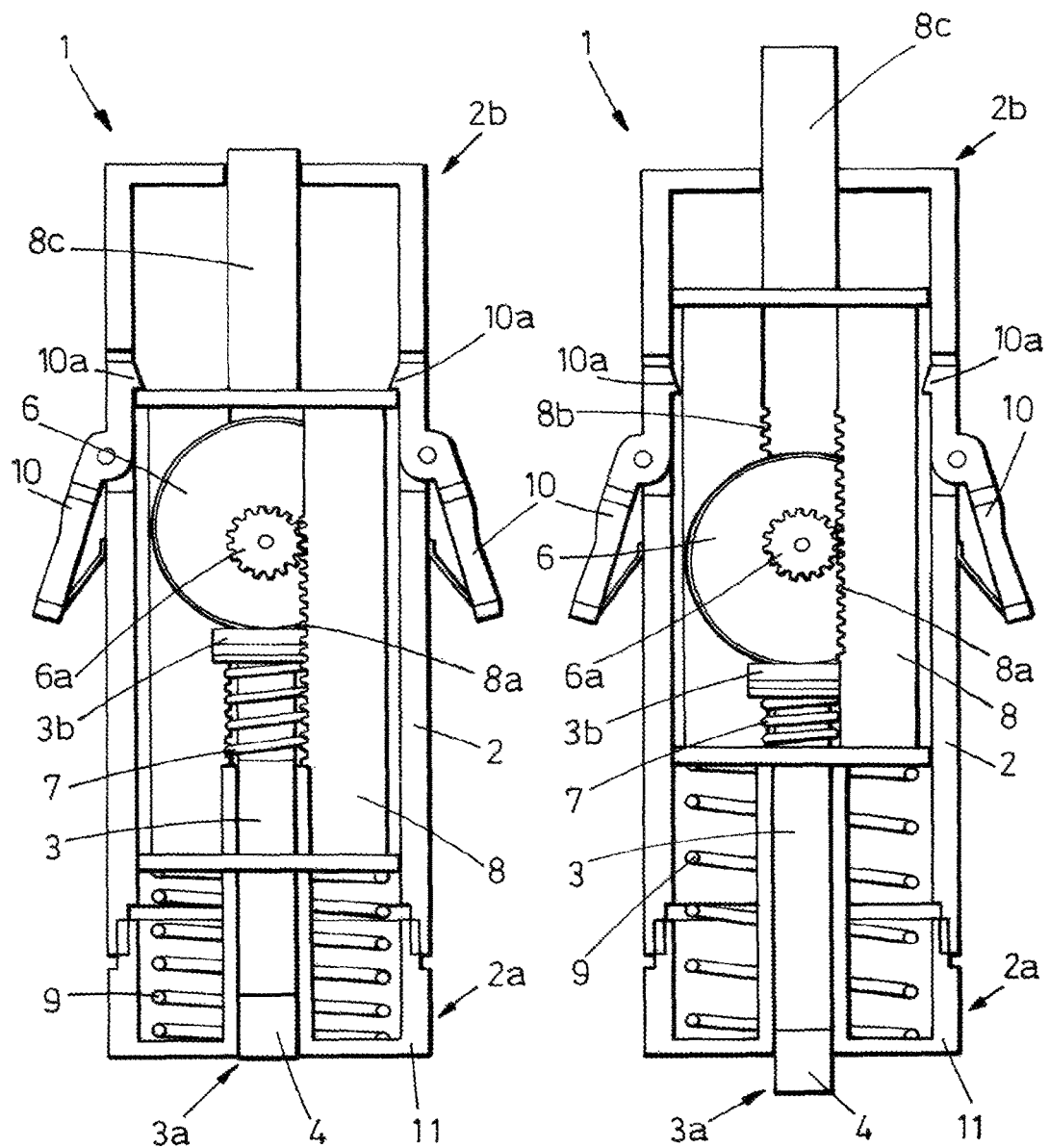
FIGS. 2a and 2b show cross-sections of the device of the invention that correspond to the first retracted position and the second extended position respectively.
Figure 3:
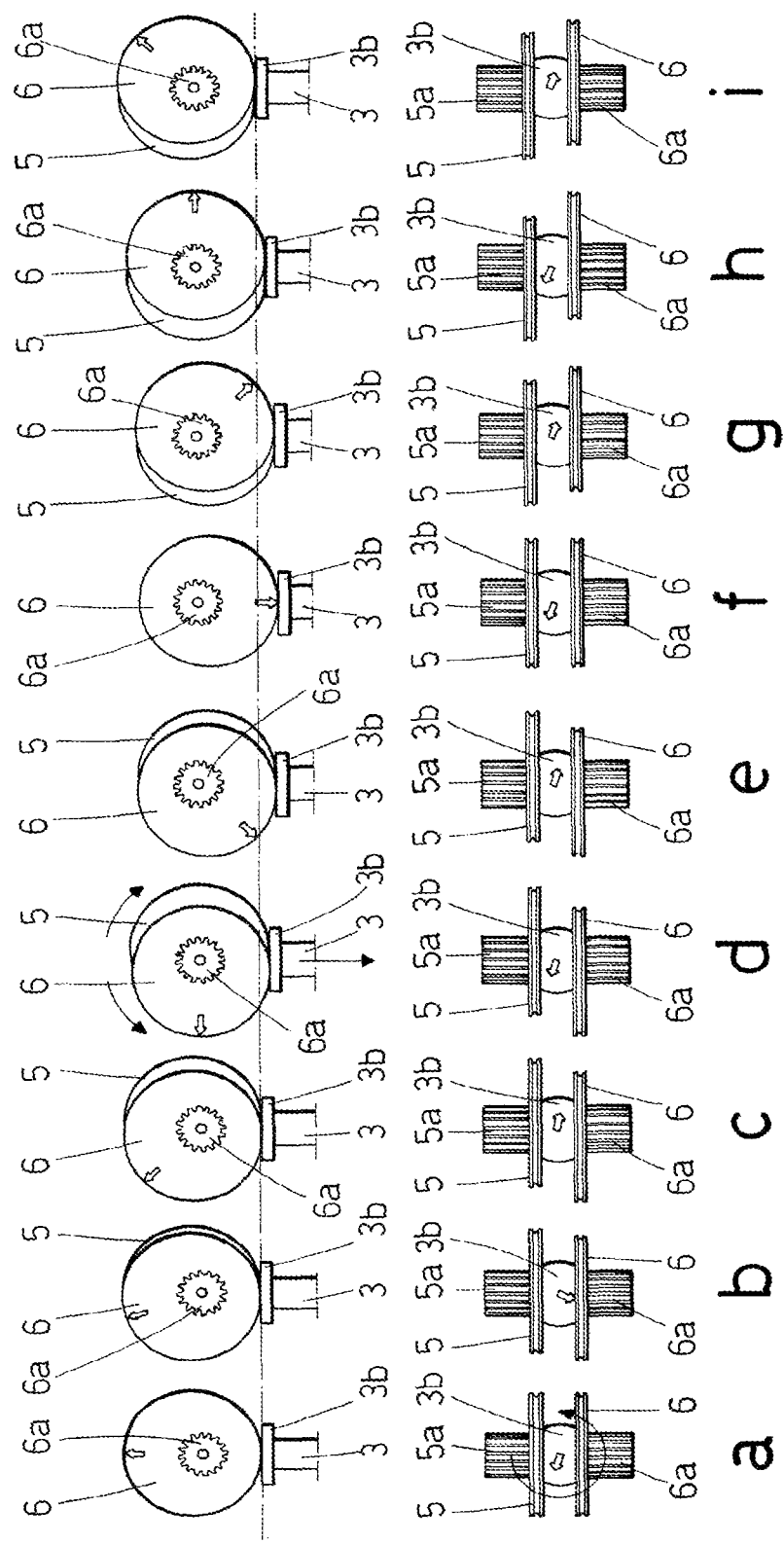
FIGS. 3a-3i show two details of the interaction between the cams and the proximal end of the rod.

The device (1) comprises an essentially cylindrical casing (2) that has a distal end (2a) and a proximal end (2b). Within the casing (2) a longitudinal rod (3) can be seen, at the distal end of which (3a) a blade (4) is fixed. The rod (3) moves longitudinally along the axis of the casing (2) from a first retracted position, which is shown in the cross-section in FIG. 2a, to a second extended position, which is shown in the cross-section in FIG. 2b, to make the blade (4) perform the cutting of the tissue, and later to withdraw again to the first retracted position.

To make the rod (3) perform the movement, the means of displacement mentioned above mainly comprise cams (5, 6) that rest on the proximal end (3b) of the rod (3). For this, in this example the proximal end (3b) of the rod (3) has a plane circular surface and the cams (5, 6) rest on said circular plane surface at two diametrically opposed points. In this way, when the cams (5, 6) are rotated in opposite directions in the way that will be explained below, the rod (3) will be caused to rotate around its own axis, thus helping to perform the cutting of the tissues with the blade (4).

The cams (5, 6) in this example have an essentially circular shape with the axis of rotation moved to one of their ends (eccentric cam). That is, in this example, the cams (5, 6) have a completely circular profile, but rotate around an axis that does not coincide with the centre of their circumference. This results in that during the first half of a turn, the distance between the axis of rotation and the proximal end (3b) of the rod (3) increases, which translates to a pushing of the rod (3) longitudinally in the distal direction toward outside the casing (2), while during the second half of the turn, this distance reduced, thus causing the return of the rod (3) in the proximal direction. In this example, to ensure the continuous contact between the cams (5, 6) and the proximal end (3b), a first spring (7) is used that has one end resting on a solid fixed part of the casing (2) and the other end resting on the lower part of the proximal end (3b) and that pushes the rod (3) in the proximal direction.

FIGS. 3a-3i show schematically the coupling between the cams (5, 6) and the proximal end (3b) of the rod (3). An arrow has been drawn on the most visible cam (6) on these figures and on the upper surface of the plane circular part that constitutes the proximal end (3b) of the rod (3) to help visualise more clearly how they rotate. The upper figures show how, as the cam (6) rotates, from left to right in the figure, pushes the rod (3) down until it reaches the lowest position in FIG. 3f, and then rises again to return to its initial position. The lower figures show how the rod (3) is forced to rotate around its axis by the cams (5, 6) because these rotate in opposite directions and rest on two diametrically opposed points on the plane surface of the proximal end (3b) of the rod (3).

In order to cause rotation of the cams (5, 6), means of actuation previously described are used, which mainly comprise an actuator (8) and a second spring (9). The actuator (8) is formed by an essentially cylindrical body that is furnished with two straight longitudinal racks (8a, 8b) arranged to mesh with pinions (5a, 6a) that project from the surface of the cams (5, 6). The second spring (9) has one end resting on the lower part of the distal end (2a) of the casing (2) and the other end resting on the lower base of the actuator (8). The effect of this configuration is that if the actuator (8) is moved longitudinally to compress the second spring (9), releasing this spring (9) causes the longitudinal rise of the actuator (8). While it is moving longitudinally upwards according to the figure, the racks (8a, 8b) of the actuator (8) cause the rotation of the pinions (5a, 6a) and therefore also the rotation of the cams (5, 6). In turn, rotation of cams (5, 6) causes the movements described above, that is, the simultaneous rotational movement of the rod (3) around its axis and longitudinal movement in the distal direction, followed by its return in the proximal direction to its initial position.

The racks (8a, 8b) and the cams (5, 6) are configured so that a complete stroke of the actuator (8) corresponds to a complete turn of the cams (5, 6) and also so that the final positions of the actuator (8) correspond to the position of the cams (5, 6) where the rod (3) is in its first retracted position. Thus for each full stroke of the actuator (8), the rod (3) starts from the first retracted position at the start of the stroke, passes to the second extended position in the middle of the stroke and finishes again in the first retracted position at the end of the stroke.

The actuator (8) of this example also has a loader (8c) that allows making a manual return of the actuator (8) to its initial position corresponding to the complete compression of the second spring (9). This loader (8c) is simply constituted by a longitudinal column that projects through the proximal end (2b) of the casing (2). Given that the size of the casing (2) allows a user to hold it with one hand, this loader (8c) is suitable for actuating with the thumb of the user.

Furthermore, to facilitate use of this device (1), a locking mechanism (10) is also included to immobilise the actuator (8) in its loaded position in which the second spring (9) is compressed and the rod (3) is in its first retracted position. This locking mechanism (10) is formed in this example by a pair of rocking latches (10) furnished with a pawl (10a) that can pass through holes in the casing (2) to engage to the actuator (8) when this is in the loaded position. Furthermore, the rocking latches (10) are configured in such a way that they tend to close on the actuator (8) by themselves, for example by means of a properly placed spring. The effect of this configuration is that when the user pushes the loader (8c) and moves the actuator (8) down according to the figure, the pawls (10a) of the rocking latch (10) automatically engage on the upper edge of the actuator (8) when this reaches its lowest position in which the second spring (9) is fully compressed, leaving the device (1) loaded for use.

Furthermore, the distal end (2a) of the casing (2) is formed in this example by a threaded part (11) screwed into the casing (2). This part (11) acts as the regulator of the distance of projection of the blade (4) in its extended position; when it is fully screwed in, the projection distance of the blade (4) is maximum, whereas as it is being screwed out, the projection distance of the blade (4) reduces. In this way, the depth of the biopsy can be regulated depending on the area of the body where it is going to be made or on any other important medical parameter. For example, it is possible that the depth of the biopsy must not be the same when it is performed on the front of a patient as when it is performed in the gluteus.

Thus, the operation of this device for making a biopsy is approximately the operation shown in FIGS. 4a-4h. It starts from the state shown in FIG. 4a in which the rod (3) is in its first retracted position where the blade (4) does not project through the distal end (2a) of the casing (2). In this example, the blade (4) is shown flush with the distal end (2a) of the casing (2), although it could be in a position further inside, depending on the position of the threaded part (11) for control. Furthermore, it can be seen how the second spring (9) is compressed and is exercising a longitudinal force upwards on the actuator (8) according to the figure.

The user takes the device (1), applies its distal end (2a) to the user's skin where the biopsy is to take place and, without releasing the pressure against the skin presses the rocking latches (10), making them rock to disengage the pawls (10a) of the actuator (8). This moment can be seen in FIG. 4b, where the actuator (8) is starting to move upwards driven by the second spring (9). This movement of the actuator (8) is transmitted via the racks (8a, 8b) to the cams (5, 6) causing their rotation, which in turn transmits to the rod (3) a rotational movement on its axis and a longitudinal movement toward the distal end (2a) of the casing (2). The blade (4) starts to emerge through the casing (2) and penetrate the skin of the patient as the cams (5, 6) rotate and push the rod (3) toward the outside, as shown in FIG. 4c.

FIG. 4d shows the second extended position in which the rod (3) projects the maximum distance from the casing (2) and therefore corresponds to the maximum depth of penetration into the patient's skin. This position corresponds to a half turn of the cams (5, 6).

From this moment, the rotation of the cams (5, 6) causes the rod (3) to move upward again, as shown in FIGS. 4e, 4f, 4g until it returns again to the first retracted position that is shown in FIG. 4h. During the whole process, the actuator (8) moves linearly upward, as shown in the figures.

The final result is the cutting of a cylindrical volume of the patient's skin. If using a blade (4) with a taper on its internal surface that narrows in the proximal direction, the penetrated cutaneous sample in the previous steps will remain stuck to the inside of the blade (4), separating from the rest of the patient's skin during the blade's retraction.

The invention claimed is:

1. An automatic device for performing skin biopsies, the device comprising:
   a casing comprising a distal end;
   a rod housed in the casing; and
   a circular blade located at the distal end of the casing;
   the device being configured for causing:
      a rotation and simultaneous longitudinal advance of the rod for changing from a first retracted position in which the blade of the rod does not project from the distal end of the casing, to a second extended position in which the blade of the rod projects from the distal end of the casing, and
      a rotation and simultaneous longitudinal retraction of said rod from the second extended position to the first retracted position;
   wherein the device further comprises:
      two parallel cams which are rotatable, in opposite directions, for contacting two diametrically opposed points of the proximal end of the rod, so that the rod is pushed by the cams, for causing advance/retraction of the rod, as well as the cams, on rotating in contact with the opposed points, provide a rotation moment upon the opposed points, which causes the rotation of the rod; and
      an actuator that causes the rotation of the cams and which is coupled to a second spring in such a way that when the rod is in the first retracted position the second spring is compressed, and on being released, the second spring causes a longitudinal movement of the actuator that is transmitted to the cams.

2. The device of claim 1 wherein the actuator comprises a longitudinal track coupled to toothed wheels mounted on the cams via a toothed rack in such a way that a longitudinal movement of the actuator is transmitted to the cams via the toothed rack.

3. The device of claim 2 wherein the cams and the actuator are designed in such a way that one full stroke of the actuator causes a full cycle of advance and retraction of the rod starting and finishing in the first retracted position.

4. The device of claim 2 wherein the actuator further comprises a loader that projects outside the casing in such a way that a user can manually move said actuator to compress the second longitudinal spring.

5. The device of claim 4, wherein the casing comprises a proximal end, wherein the loader projects in a longitudinal direction through the proximal end of the casing.

6. The device of claim 4 further comprising a locking mechanism mounted on the case, so as to engage with the actuator when the actuator compresses the second longitudinal spring.

7. The device of claim 6 wherein the locking mechanism comprises two rocking latches furnished with a pawl for engaging with the actuator.

8. The device of claim 7, wherein the case is provided with holes through which the pawl can pass to engage to the actuator when the actuator is in the loaded position.

9. An automatic device for performing skin biopsies, the device comprising:
   a casing comprising a distal end;
   a rod, housed in the casing; and
   a circular blade, located at the distal end of the casing;
   the device being configured for causing:
      a rotation and simultaneous longitudinal advance of the rod for changing from a first retracted position in which the blade of the rod does not project from the distal end of the casing to a second extended position in which the blade of the rod projects from the distal end of the casing, and
      a rotation and simultaneous longitudinal retraction of the rod from the second extended position to the first retracted position;
   wherein the device further comprises:
      two parallel cams which are rotatable, in opposite directions, for contacting two diametrically opposed points of the proximal end of the rod, so that the rod is pushed by the cams, for causing advance/retraction of the rod, as well as the cams, on rotating in contact with the opposed points, provide a rotation moment upon the opposed points, which cause the rotation of the rod;
      a first longitudinal spring for pushing the rod in the proximal direction, maintaining the cams and the opposed points of the proximal end of the rod in contact; and
      actuation means for automatically acting on the cams and the first longitudinal spring so as to cause the longitudinal advance and retraction of the rod.

* * * * *